United States Patent [19]
Cadwell

[11] Patent Number: 5,566,678
[45] Date of Patent: Oct. 22, 1996

[54] DIGITAL EEG NOISE SYNTHESIZER

[75] Inventor: John A. Cadwell, Richland, Wash.

[73] Assignee: Cadwell Industries, Inc., Kennewick, Wash.

[21] Appl. No.: 369,270

[22] Filed: Jan. 5, 1995

Related U.S. Application Data

[63] Continuation of Ser. No. 119,955, Sep. 10, 1993.

[51] Int. Cl.⁶ .................................................. A61B 5/04
[52] U.S. Cl. ........................ 128/731; 128/732; 128/733
[58] Field of Search .................................. 128/731, 732, 128/733

[56] References Cited

U.S. PATENT DOCUMENTS

| | | | |
|---|---|---|---|
| 3,621,836 | 11/1971 | Nagatomi | 128/731 |
| 3,774,593 | 11/1973 | Hakata et al. | 128/731 |
| 3,892,227 | 7/1975 | Coursin et al. | 128/731 |
| 3,947,974 | 4/1976 | Gordon et al. | 35/17 |
| 3,994,282 | 11/1976 | Moulet | 128/1 C |
| 4,417,592 | 11/1983 | John | 128/731 |
| 4,454,886 | 6/1984 | Lee | 128/732 |
| 4,777,952 | 10/1988 | Pavel | 128/419 S |
| 4,873,981 | 10/1989 | Abrams et al. | 128/419 S |
| 4,883,067 | 11/1989 | Knispel et al. | 128/732 |
| 4,928,704 | 5/1990 | Hardt | 128/732 |
| 4,984,578 | 1/1991 | Keppel et al. | 128/732 |

*Primary Examiner*—Angela D. Sykes
*Assistant Examiner*—Stephon Huang
*Attorney, Agent, or Firm*—Christensen, O'Connor, Johnson & Kindness PLLC

[57] ABSTRACT

A method and apparatus for generating an audio accompaniment for digital EEG systems (electroencephalographs) is disclosed. In the past, EEG systems included pen-on-paper EEG recorders to trace a representation of sensed brain wave activity on a strip of paper. This produced varying amounts of auditory noise that corresponded to the amount of brain wave activity which was used by medical technicians monitoring a patient. Digital EEG systems create traces on non-auditory (i.e., CRT) displays. As a result, the auditory feedback provided by the movement of pens on paper and the associated medical benefits have been lost. The invention remedies this problem by providing a method and apparatus that analyzes EEG signals and mimics the sounds that would have been created by the prior art pen-on-paper EEG recorders if the signals had been applied in analog form to such recorders. The invention includes several different synthesizers that replicate the sounds of pens moving across recorder paper, pens hitting on one another, and the motor drive train of a pen-on-paper EEG recorder. The system constantly analyzes the incoming EEG signals and updates control signals that control the synthesizers in a way that ensures that the sounds produced closely approximate the sounds of an equivalent pen-on-paper EEG system.

11 Claims, 6 Drawing Sheets

DIGITAL EEG NOISE SYNTHESIZER

This application is a continuation application based on prior copending application Ser. No. 08/119,955, filed on Sep. 10, 1993.

FIELD OF THE INVENTION

This invention relates generally to noise synthesizers, and more particularly to a noise synthesizer for a digital EEG recorder that can mimic the sounds generated by a mechanical pen-on-paper EEG recorder.

BACKGROUND OF THE INVENTION

The primary medical instrument used to monitor the electrical activity of a patient's brain is the electroencephalograph (EEG). EEGs monitor brain activity by measuring the very small voltage fluctuations that are generated in the brain, which are detected by electrodes attached to a patient's scalp. To aid in studying these analog signals, a record of the voltage fluctuations (called an electroencephalogram) is often made over time. Traditionally, electroencephalograms are made using a mechanical EEG recorder that employs pens to record the analog voltage fluctuations on a strip of paper. As a continuous chart of paper is moved beneath an array of 10 to 24 galvanometer-driven ink pens, the pens trace out the brain wave activity as a series of wavy or jagged lines.

As a by-product of the recording process, pen-on-paper EEG recorders produce a significant amount of auditory noise. Most of the noise is produced by the pens of the recorder, which generate distinctive sounds as they sweep back and forth across the paper and collide with each other or with mechanical stops. A lesser amount of noise is produced by the paper feed mechanism, which emits a continuous "hum." The total noise generated by a pen-on-paper EEG recorder depends upon the electrical activity of the brain of the patient plus artifact from muscle or electrode movement. When a patient moves or has heightened levels of brain activity, the sound generated by the pens' movement increases. When a patient is quiet and exhibits very little EEG activity, the continuous sound of the paper feed mechanism generates most of the noise.

Experienced medical technicians use the sounds produced by pen-on-paper EEG recorders to their advantage. Because the sound produced by such recorders is directly related to the incoming signals, technicians can correlate distinctive pen noises with changing brain wave patterns. For example, certain high amplitude brain activity such as epileptiform discharges (without seizure activity) will cause a pen-on-paper EEG recorder to produce a characteristic sound signature. As a result, medical technicians monitoring a patient can therefore rely on recorder sounds for information regarding the patient's mental state rather than continuously observing the output traces produced by the recorder. This allows the technicians to visually monitor the patient while aurally monitoring electrical brain activity.

In recent years, analog EEGs and their associated mechanical pen-on-paper recorders have begun to be replaced by EEGs that process electroencephalogram signals digitally. Digital EEGs convert the analog brain waves into digital signals that are stored in digital form in computer memory, or on computer disk or tape. The digital data is displayed as brain wave traces on a video screen. Such systems are nearly silent, thus depriving trained medical technicians of a valuable source of information. Even when the digitally stored information is printed out using a dot-matrix printer, a thermal printer or a laser printer, sounds comparable to those created by pen-on-paper EEG recorders are not created. Further, because these sounds are absent, medical technicians are forced to watch the screen of the display rather than watch the patient. Thus, medical technicians may miss information they would have obtained if they had been observing a patient during a critical interval.

The present invention is directed to overcoming the foregoing disadvantage by adding the characteristic audible sounds of a pen-on-paper EEG recorder to the visual output of digital EEGs. As a result, digital EEG systems incorporating the invention will provide the same (or better) information than that provided by prior analog EEG systems. That is, the sounds produced may take one, or both, of two forms. They may mimic the sounds of moving pens on paper, exactly reproducing the sound that a pen-on-paper EEG recorder attached to an analog EEG would make if receiving the same brain wave signals. Or the sounds may be new and perhaps more distinctive to correlate with changing brain wave patterns.

SUMMARY OF THE INVENTION

In accordance with this invention, a method and apparatus for synthesizing noises that mimic the sounds of a pen-on-paper EEG recorder are provided. In accordance with the invention three component synthesizers, each designed to reproduce a characteristic sound produced by a pen-on-paper EEG recorder, are provided. The component synthesizers closely mimic the sounds: (i) of a pen moving across paper; (ii) of a pen colliding with another pen or with a mechanical stop; and (iii) of a paper feed mechanism.

In accordance with another aspect of this invention, the synthesizers are designed to work in conjunction with a digital EEG recorder. Incoming digital signals are manipulated digitally to determine the path of travel the pen of an equivalent pen-on-paper EEG recorder would take if the analog signal from which the digital signal is derived were applied to such a recorder. Preferably, all signal processing and noise synthesis is performed using digital noise generators and filters. The signals produced by the component synthesizers are combined and the composite noise signal is converted from digital form to analog form, amplified, and output through a loudspeaker.

In accordance with yet another aspect of this invention, the processing of the sound (starting with manipulation based on the original EEG signal and ending with audio synthesis) takes place in real time. Thus, the invention accurately creates the sound of an equivalent pen-on-paper EEG recorder as the corresponding signals are recorded and/or displayed.

As will be readily appreciated from the foregoing summary, the present invention reduces the need for a medical technician to visually monitor a patient's EEG traces on the display of a digital EEG system because the invention allows a technician to use auditory feedback to keep apprised of the general brain wave activity of the patient in the same way as was previously done by technicians using analog EEG systems.

BRIEF DESCRIPTION OF THE DRAWINGS

The foregoing aspects and many of the attendant advantages of this invention will become more readily appreciated as the same becomes better understood by reference to the following detailed description of a preferred embodiment of the invention, when taken in conjunction with the accompanying drawings, wherein.

DETAILED DESCRIPTION OF THE PREFERRED EMBODIMENT

Figure 1:
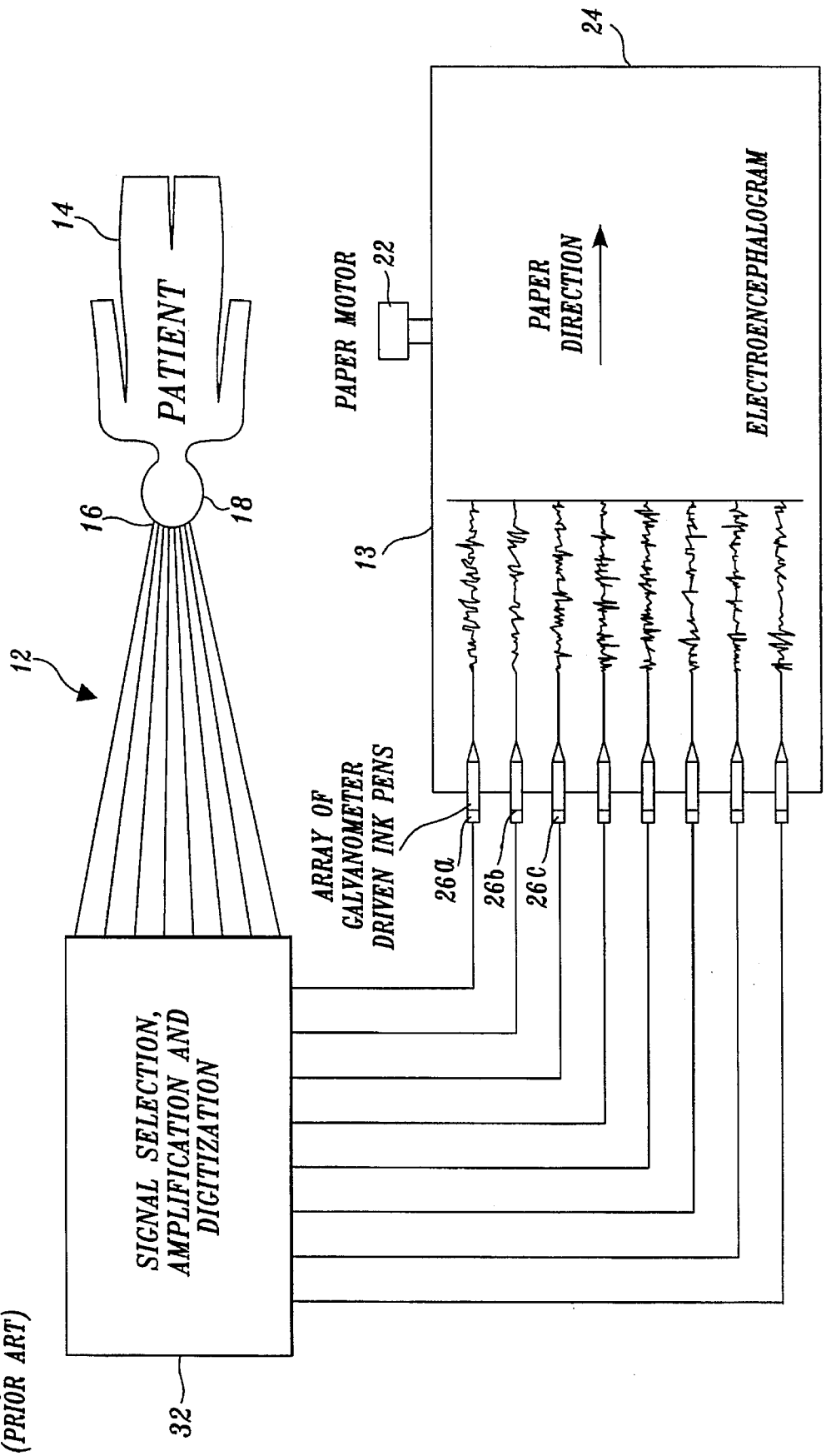
FIG. 1 is a pictorial representation of a prior art EEG system that includes a pen-on-paper recorder for creating EEG traces on a scrolling paper chart with galvanometer-driven ink pens.

FIG. 1 is a pictorial representation of a prior art analog EEG system 12 that includes pen-on-paper EEG recorder 13 connected to a patient 14. EEG signals are detected by electrodes 16 that are attached to a patient's head 18 in a manner well known to EEG technicians. The minute voltage signals detected by the electrodes 16 are selected and electronically amplified by a signal selection and amplification circuit 20. The determination of which signals are to be selected and amplified is made by an EEG technician adjusting switches (not shown). The selected signals are applied to an array of galvanometer-driven ink pens 26a, 26b, 26c . . . During operation, a paper motor 22 continuously pulls chart paper 24 beneath the array of ink pens 26a, 26b, 26c . . . as the ink pens are driven by galvanometers that respond to voltage changes in the EEG signals. As the paper 24 scrolls beneath the pens, each ink pen 26a, 26b, 26c . . . traces out the EEG signal detected by its associated electrode pair 16. Thus, a set of wavy or jagged lines 28a, 28b, 28c . . . is produced. This recording process creates a significant amount of acoustic noise, including the sound of the ink pens 26a, 26b, 26c . . . tracing across the paper chart 24, the sound of the ink pens 26a, 26b, 26c . . . colliding with each other or with mechanical stops, and the continuous sound of the paper motor 22 pulling the paper across the recording surface lying beneath the ink pens 26a, 26b, 26c . . .

Figure 2:
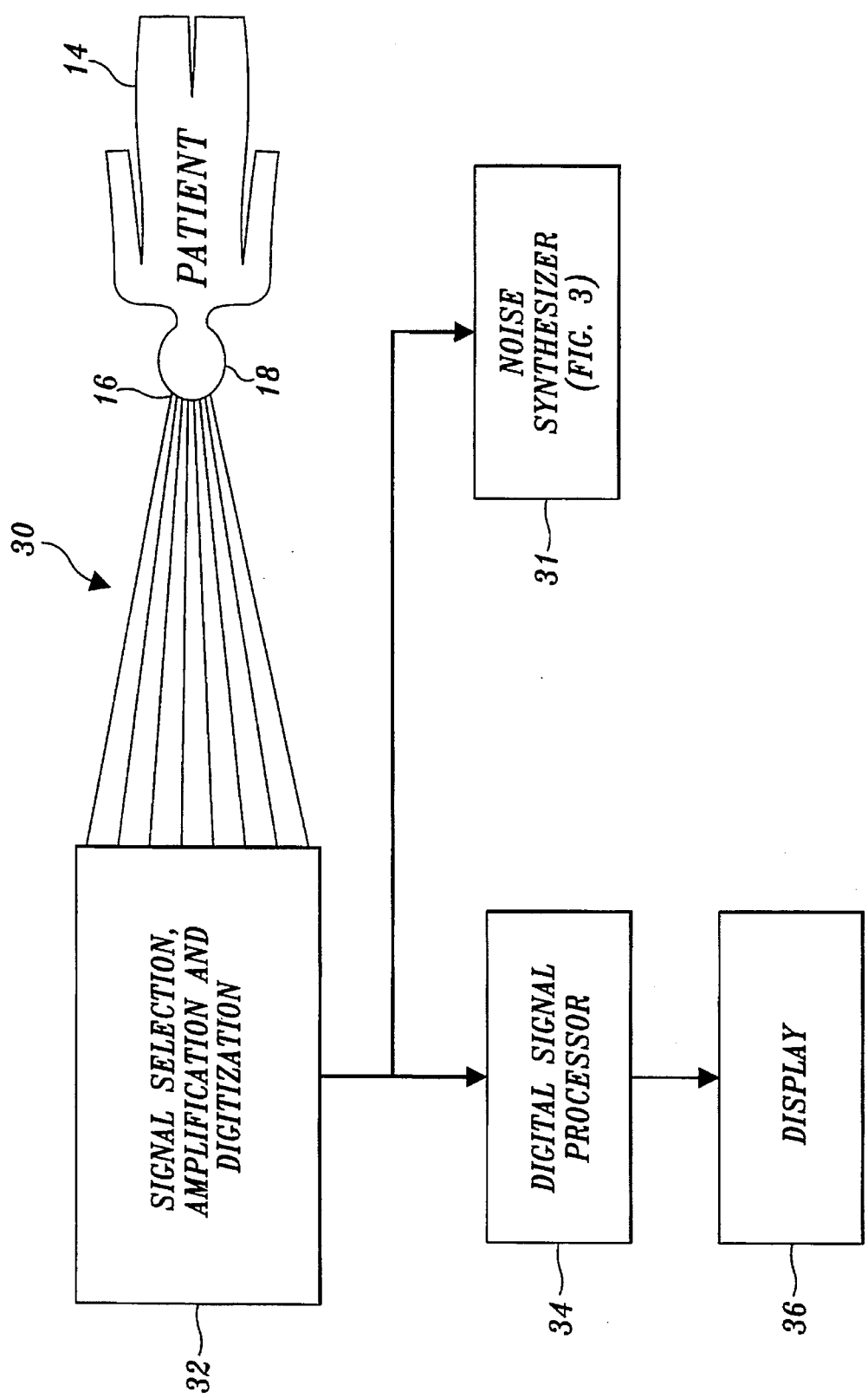
FIG. 2 is a functional block diagram of a digital EEG system incorporating a digital EEG noise synthesizer formed in accordance with this invention.

The present invention is directed to providing a noise synthesizer 31 that mimics the sounds of a pen-on-paper EEG recorder 13 of the type pictorially depicted in FIG. 1. More specifically, as shown in FIG. 2, functionally, a digital EEG system 30 includes a signal selection, amplification, and digitization circuit 32 that receives the analog signals detected by the electrodes 16, selects one or more of the signals to be digitized and digitizes the selected signals. The digitized signals are received by a digital signal processor 34, which may take the form of a suitably programmed personal computer. In addition to analyzing the signals in accordance with algorithms that do not form a part of this invention, the digital signal processor 34 converts the received digital signals into a form suitable for creating an analog representation of the original analog signals detected by the electrodes 16 on a display 36. In accordance with this invention a digital EEG system is modified by adding a noise synthesizer 31 that receives the digitized electrode derived signals and creates noise that replicates the noise that would have been created if the electrode signals had been applied to a pen-on-paper EEG recorder 13 in the manner illustrated in FIG. 1 and described above.

Figure 3:
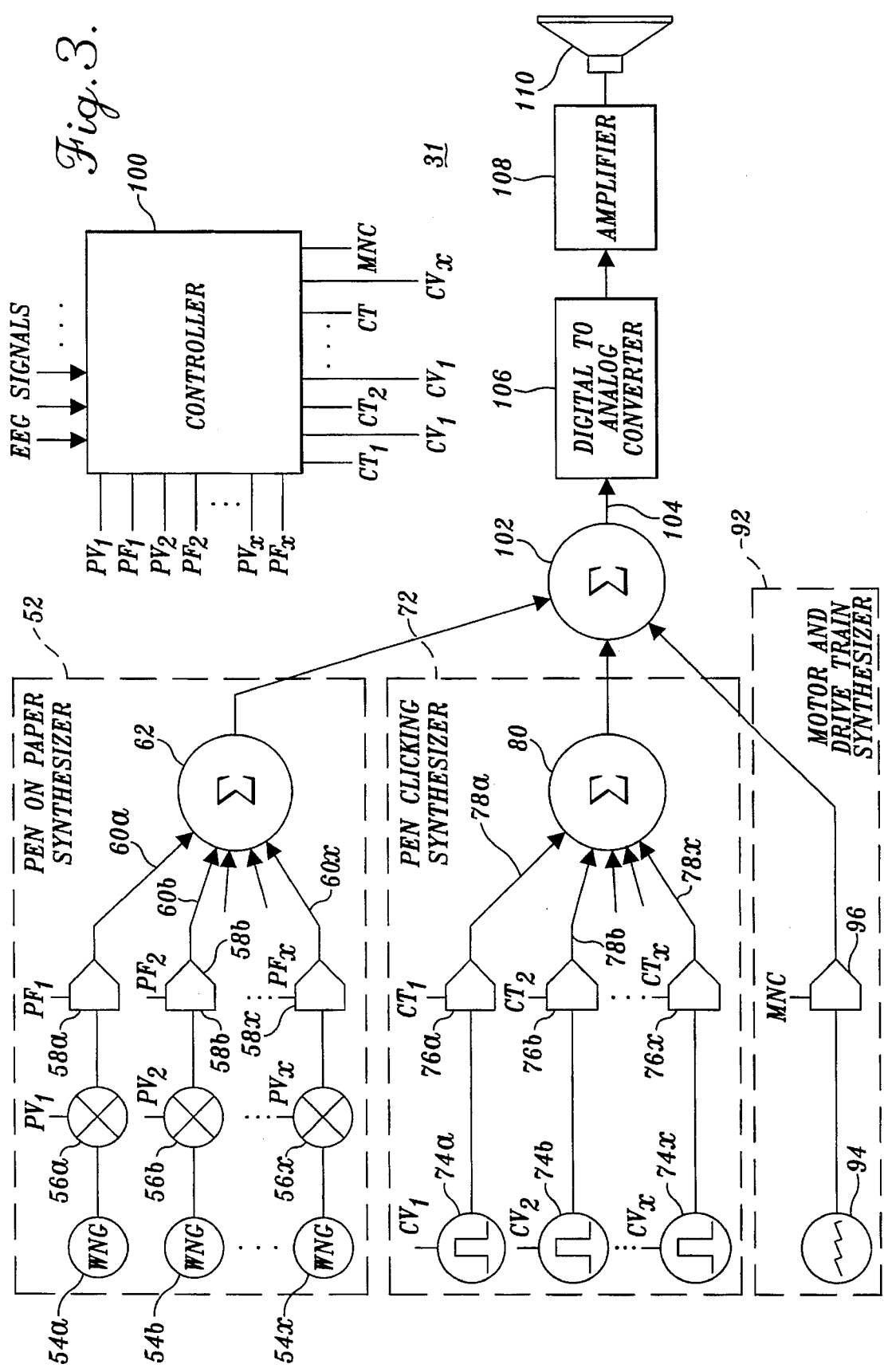
FIG. 3 is a block diagram of a digital EEG noise synthesizer formed in accordance with the present invention.

FIG. 3 is a block diagram of a noise synthesizer formed in accordance with the invention suitable for creating the sound of a traditional pen-on-paper EEG recorder. While illustrated in functional block form, preferably the noise synthesizer is implemented in a microprocessor form that includes suitable commercially available digital signal processing chips.

Conceptually, the noise synthesizer can be viewed as three component synthesizers, each of which produces a sound that is characteristic of a certain aspect of the noise produced by a pen-on-paper EEG recorder. The three component synthesizers are a pen-on-paper synthesizer 52, a pen-clicking synthesizer 72, and a motor and drive train synthesizer 92. In addition to the component synthesizers, the noise synthesizer illustrated in FIG. 3 includes: a controller 100; a noise component summer 102; a digital-to-analog (D/A) converter 106; an amplifier 108; and a speaker 110. The controller 100, which forms the main part of the digital signal processor (DSP), is microprocessor based, i.e., the controller includes a microprocessor, random access memory, read only memory and suitable interface and support elements, all well known to those skilled in the DSP art.

The pen-on-paper synthesizer 52 recreates the sound of pens moving across paper. The pen-on-paper synthesizer includes a plurality of noise channels 60a, 60b . . . 60x and a channel summer 62. Each of the noise channels 60a, 60b . . . 60x includes a white noise generator (WNG) 54a, 54b . . . 54x; a multiplier 56a, 56b . . . 56x; and a low pass filter 58a, 58b . . . 58x. The outputs of the white noise generators 54a, 54b . . . 54x are applied to the multipliers 56a, 56b . . . 56x, respectively, where they are multiplied by pen volume signals ($PV_1$, $PV_2$ . . . $PV_x$) produced by the controller in the manner hereinafter described. The outputs of the multipliers 56a, 56b . . . 56x are each filtered by one of the low pass filters 58a, 58b . . . 58x. The cutoff frequencies of the low pass filters are determined by pen frequency control signals ($PF_1$, $PF_2$ . . . $PF_x$) produced by the controller 100 in the manner hereinafter described. The outputs of the noise channels formed by the white noise generators 54a, 54b . . . 54x, the multipliers 56a, 56b . . . 56x, and the low pass filters 58a, 58b . . . 58x are summed together by the summer 62.

As will be better understood from the following description of the operation of the program (FIG. 5) that controls the operation of the controller 100, the pen volume control signals $PV_1$, $PV_2$ . . . $PV_x$ and the pen frequency control signals $PF_1$, $PF_2$ . . . $PF_x$ are EEG channel related. That is, the pen volume and pen frequency control signals associated with each noise channel 60a, 60b . . . 60x are derived from the same EEG electrode channel. While the number of noise channels 60a, 60b . . . 60x could be chosen to equal the number of EEG electrode channels, it has been experimentally determined that generating the sound produced by the eight (8) loudest channels is sufficient to closely reproduce the sound of a mechanical recorder. By loudest is meant the channels producing signals that would create the greatest pen movement and, thus, the greatest pen noise if applied in analog form to the galvanometers of a pen-on-paper EEG recorder. Synthesizing the sound of additional pens does not produce any significant improvements in the overall sound quality.

The pen-clicking synthesizer 72 produces the sound of pens colliding with one another or with a mechanical stop. This sound has been experimentally determined to resemble a type of "click." The pen-clicking synthesizer comprises a plurality of click generating channels 78a, 78b ... 78x and a summer 80. Each of the click generator channels 78a, 78b ... 78x includes a pulse generator 74a, 74b ... 74x and a low pass filter 76a, 76b ... 76x. The pulse generators produce a pulse when triggered. The amplitude of the pulses is controlled by a channel related click volume control signal $CV_1, CV_2 ... CV_x$. The click volume control signals, which also function as trigger signals, are produced by the controller 100 in the manner hereinafter described. The output of each of the pulse generators 74a, 74b ... 74x is applied to a respective one of the low pass filters 76a, 76b ... 76x in the manner described below with respect to FIG. 4. The cutoff frequencies of the low pass filters 76a, 76b ... 76x are controlled by click timbre control signals $CT_1, CT_2 ... CT_x$, which are also produced by the controller 100 in the manner hereinafter described. The outputs of the low pass filters 76a, 76b ... 76x are summed by the summer 80.

As will be better understood from the following description of the operation of the program (FIG. 5) that controls the operation of the controller 100, the click volume and click control signals $CV_1, CV_2 ... CV_x$ and $CT_1, CT_2 ... CT_x$ are EEG channel related. That is, the click volume and click timbre control signals are related to the EEG channels whose EEG signal strength is such that if applied to the galvanometers of a pen-on-paper EEG recorder would cause the pens to create a clicking noise by hitting a stop. While the number of noise channels 78a, 78b ... 78x could be chosen to equal the number of EEG signal channels, as with the pen noise synthesizer, it has been experimentally determined that a more limited number of click noise channels 78a, 78b ... 78x are adequate to create the "clicking" sounds of an entire array of ink pens 26 with high accuracy. Specifically, it has been found that four click generator channels are adequate, when used sequentially, even though more can be included if desired.

As will be better understood from the following description of the program (FIG. 5) that controls the operation of the controller 100, the click volume (CV) signals both trigger and control the magnitude of a pulse produced by the associated pulse generator 74a, 74b ... 74x. The click timbre (CT) signals control the ringing frequency of the associated low pass filter 76a, 76b ... 76x such that when a pulse is applied to a filter in the manner described below, a digital signal suitable for creating a decaying sinusoid when convened to analog form is created by the filter. The frequency of the decaying sinusold sounds like the click that occurs when the pen of a pen-on-paper EEG recorder hits a stop or another pen.

The motor and drive train synthesizer 92 reproduces the sound of the motor and drive train noise. The base noise of a pen-on-paper EEG recorder's paper feed mechanism has experimentally been determined to be a 50 or 60 Hz tone with overlying harmonics slightly modulated at 0.2 to 0.5 Hz. Since a tone of this low a frequency is below the normal hearing threshold of a human, it has been found that reproducing the third harmonic of the fundamental frequency suitably approximates the human understood portion of the paper feed mechanism. The motor and drive train synthesizer uses a sawtooth generator 94 and a filter 96 to create this fundamental. More specifically, the sawtooth generator produces a sawtooth signal having a frequency in the third harmonic range—200 Hz, for example. The sawtooth signal is filtered by the filter 96. The cutoff frequency of the filter is controlled by a motor noise coefficient (MNC) signal produced by the controller in the manner described below.

While other types of filters may be used, at present, the preferred filters for use in all of the component synthesizers shown in FIG. 3 are digital 2-pole elliptic IIR filters. While the nature of the filters is the same, their coefficient values and manner of operation varies depending upon the channel in which the filter is used. As a matter of fact, the filters 76a, 76b ... 76x included in the pen-clicking synthesizer channels function more as decaying sinusoidal oscillators rather than signal filters. The following description describes a generic digital 2-pole elliptic IIR filter, followed by a description of how the generic filter is configured for use in each of the component synthesizers.

Figure 4:
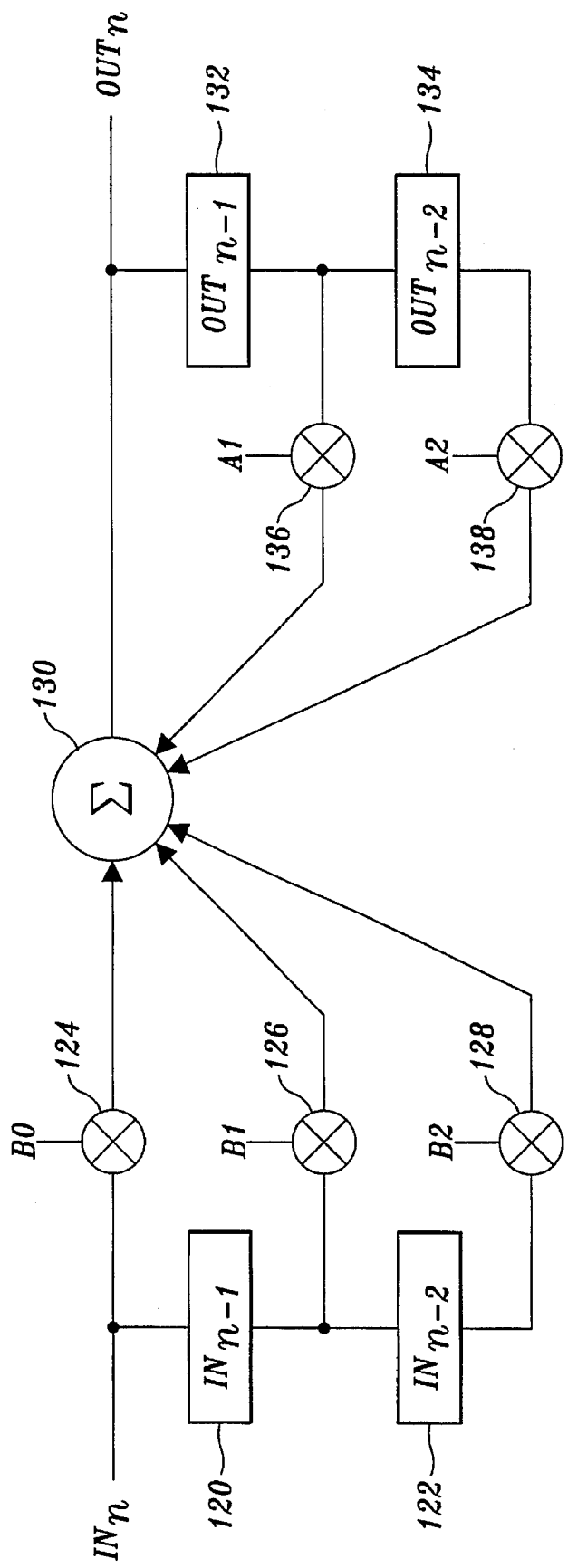
FIG. 4 is a block diagram of a digital 2-pole elliptic IIR filter suitable for use in the noise synthesizer illustrated in FIG. 3.

A functional diagram of a generic digital 2-pole elliptic IIR filter is shown in FIG. 4. The illustrated digital 2-pole elliptic IIR filter includes: two input delay lines 120 and 122; three input multipliers 124, 126 and 128; a summer 130; two output delay lines 132 and 134; and two output multipliers 136 and 138. Filter coefficients designated B0, B1 and B2 are applied, respectively, to one input of each of the three input multipliers 124, 126 and 128; and filter coefficients designated A1 and A2 are applied, respectively, to one input of each of the two output multipliers 136 and 138. The bits of the digital input signal ($IN_n$) to be filtered are applied to the first input delay line 120 and to the other input of the first input multiplier 124. The output of the first input delay line 120 is applied to the input of the second input delay line 122 and to the other input of the second input multiplier 126. The output of the second input delay line 122 is applied to the other input of the third input multiplier 128. The outputs of the input multipliers 124, 126 and 128 are applied to inputs of the summer 130. The output of the summer 130, which is the output ($OUT_n$) signal of the filter, is applied to the input of the first output delay line 132. The output of the first output delay line 132 is applied to the other input of the first output multiplier 136 and to the input of the second output delay line 134. The output of the second output delay line is applied to the other input of the second output multiplier 138. The outputs of the first and second output multipliers 136 and 138 are applied to other inputs of the summer 130.

When a 2-pole elliptic IIR filter of the type shown in FIG. 4 is used as the filter 58a, 58b ... 58x in one of the channels 60a, 60b ... 60x of the pen-on-paper synthesizer 52, all of the filter coefficients—A1, A2, B0, B1, and B2—are set to the related pen frequency value $PF_1, PF_2 ... PF_x$ determined by the controller 100 in the manner described below.

When a 2-pole elliptic IIR filter of the type shown in FIG. 4 is used as the filter 76a, 76b ... 76x in one of the channels 78a, 78b ... 78x of the pen-clicking synthesizer, the coefficient values B0, B1, and B2 are set to zero (0). Coefficient A1 is set to the related click timbre value $CT_1, CT_2 ... CT_x$ determined by the controller 100 in the manner described below. Coefficient A2 is set to a fixed value. Further, instead of being applied to the input ($IN_n$) of the filter, the click volume controlled pulses are applied to the input of the second output delay line 134. This forces the filter to ring, i.e., produce a damped sinusoidal output, at a frequency that closely approximates the sound of a click of the type produced by pen-on-paper EEG recorders of the type shown in FIG. 1 and described above.

When a 2-pole elliptic IIR filter of the type shown in FIG. 4 is used as the filter 96 of the motor and drive train synthesizer 92, all of the coefficients except for A1 are fixed.

Coefficient A1 is set to the motor noise constant (MNC) value determined by the controller 100 in the manner described below.

Returning to FIG. 3, the three noise components generated by the pen-on-paper synthesizer 52, the pen-clicking synthesizer 72, and the motor and drive train synthesizer 92 that replicate the noise generated by a pen-on-paper EEG recorder are applied to the summer 102. The summer 102 sums the outputs of the synthesizers and generates a composite digital noise signal 104. The composite digital noise signal 104 is applied to the D/A converter 106 which converts the signal to analog form. The analog signal is amplified by the amplifier 108, and output to a listener via the speaker 110. In this manner, a continuous audible signal is generated that simulates the sounds produced by a traditional pen-on-paper EEG recorder.

As noted above, FIG. 5 is a flowchart of the program that controls the operation of the controller 100 in a way that enables the noise synthesizer 31 to mimic the sounds of a pen-on-paper EEG recorder. In general, based on the EEG signals received from the electrodes, the program causes the controller 100 to compute the speed of movement of the pens of a pen-on-paper EEG recorder would have if the EEG signals were applied to such a recorder and use the resulting data to calculate control signals that control the operation of the pen-on-paper, pen-clicking and motor and drive train synthesizers 52, 72 and 92 so that they reproduce the appropriate sound.

Figure 5:
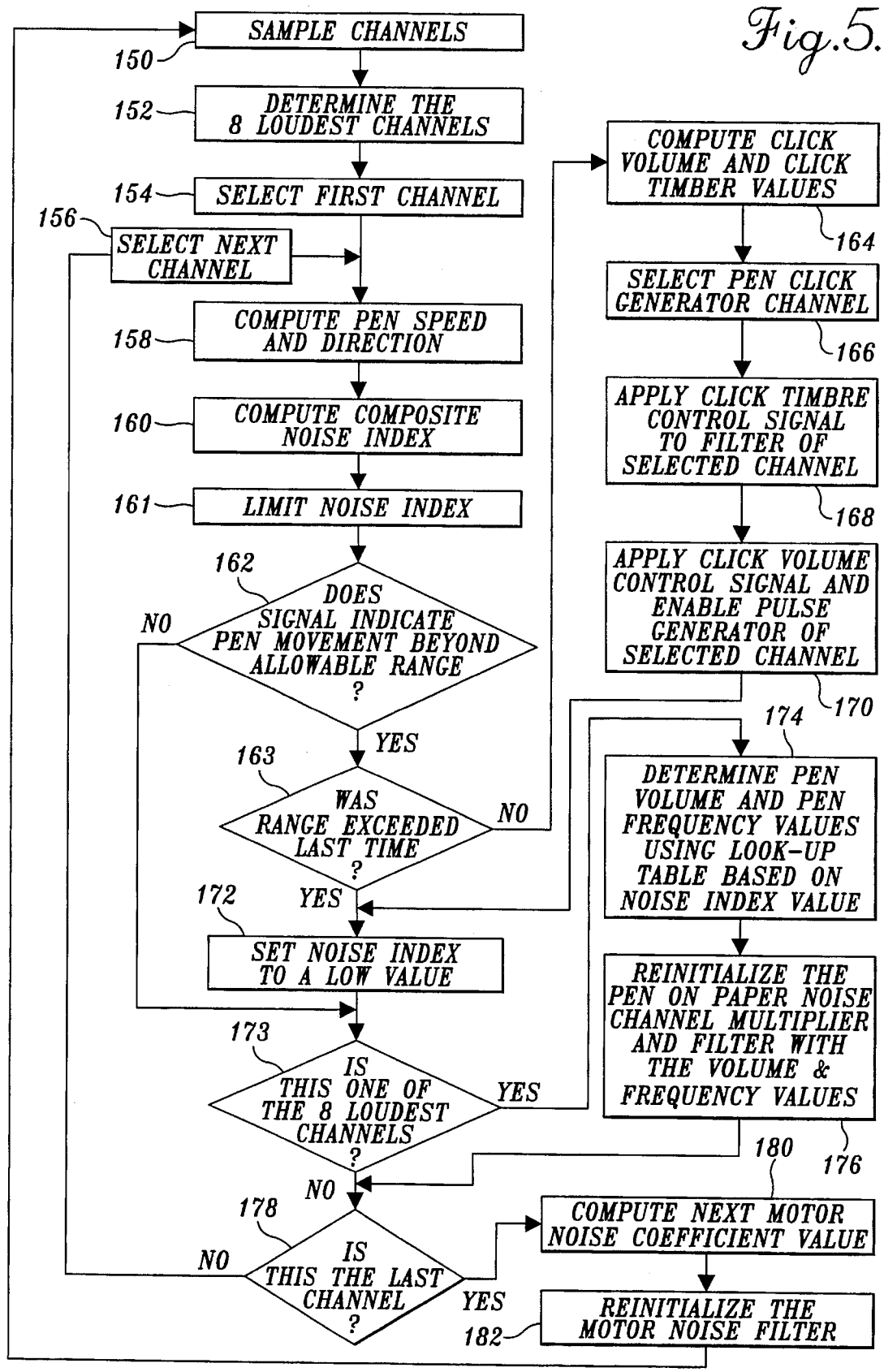
FIG. 5 is a flow chart of a method of programming a digital EEG noise synthesizer to operate according to the present invention.

As shown in FIG. 5, all incoming EEG signal channels are digitally sampled at a suitable rate, such as 200 times a second (block 150). Thus, each sample comprises a set of data points that track the amplitude of each EEG signal channel. Rather than produce the sounds that would be generated if all of the EEG signals were applied to a pen-on-paper EEG record, as noted above, preferably only the sounds that would be created by the eight "loudest" channels are produced. Thus, at block 152, the program compares the sets of data samples to determine the eight loudest channels, i.e., the eight channels whose signals have the greatest amplitude. After identifying the eight loudest channels, the program selects the first channel to synthesize (block 154). The first channel could be the loudest channel or the first channel in a numerical sequence that includes the eight loudest channels. The program then enters the main program loop.

Next, the program determines from the channel signal information how fast and in what direction the pen of a pen-on-paper EEG recorder would move if the original EEG signal were applied to the pen of such a recorder. Specifically, the program calculates the speed of the pen by comparing the current EEG data points with those measured by the previous sample (block 158). The program then computes a composite noise index that is proportional to the calculated pen speed (block 160), using the equation noise index=1.25 k (pen speed) for positive excursions and the equation noise index=0.75 k (pen speed) for negative excursions, where k lies in the range 0.0005 to 0.005 (preferably 0.0013); and pen speed is in microvolts/sec. The value of noise index is then limited (block 161) to some acceptable range, such as between 0 and 27, i.e., 0≦noise index≦27. This provides a maximum noise index at pen speeds of approximately 20,000 μv/sec, when a 200 sample/sec update rate is used.

At decision block 162, the program checks to see if a pen driven by the channel signal would have moved beyond an allowable range of motion. As will be understood by those familiar with pen-on-paper EEG recorders, pens remaining within a predetermined range do not collide with one another or with mechanical stops. Those that do usually collide with one another or with a mechanical stop. If the test reveals that a pen driven by the signal would have exceeded the allowable range, a test is made (decision block 163) to determine if the range was exceeded the last time this channel signal was analyzed. If the allowable range was not exceeded and if the range was not exceeded the last time, the program proceeds to the click subroutine because these decisions mean that a pen driven by the same signal would either have hit a mechanical stop or another pen and that this is the first time the hit was detected, the program shifts to a "click" subroutine. The first step in the click subroutine (block 164) is to compute click volume ($CV_i$) and click timbre ($CT_i$) control signal values. These values are determined from the following equations:

$$CV_i = k_4 + (k_5 * \text{noise index})$$

$$CT_i = k_6 + (k_7 * \text{noise index})$$

where: k4 lies on the range 0.2 to 0.4 (preferably 0.375)

where: k5 lies on the range 0.02 to 0.03 (preferably 0.023)

where: k6 lies on the range 2000 to 3000 (preferably 2500)

where: k7 lies on the range 30 to 60 (preferably 55)

CV has a minimum value of zero (0) and a maximum value of one (1). CT is the 3 dB rolloff frequency. For a 12 kHz data sampling rate, the A2 coefficient of the 2-pole elliptic IIR is set to −1.5 and the A1 coefficient is set equal to 0.5+0.0046 * noise index. As noted above, the B0, B1 and B2 coefficient values are all set to zero.

The subroutine then selects the channel 78a, 78b ... 78x of the pen-clicking synthesizer 72 to generate the dick (block 166). After selecting the pen click generator channel 78a, 78b ... 78x, the subroutine sets the click filter frequency by applying the click timbre control signal ($CT_i$) to the filter of the selected channel (block 168). Then the tinging of the selected click generator channel is started by applying the click volume control signal ($CV_i$) to the pulse generator of the selected channel and enabling the pulse generator (block 170).

Next, at block 172, the subroutine resets the calculated noise index to a low value, e.g., zero. Because the noise index has been set low, the sound of a pen moving across paper is greatly reduced from what it would have been when sounds are produced in the manner described below. This replicates the sound of a pen-on-paper EEG recorder when a click occurs, because the pen is momentarily stopped when it rests against the mechanical stop.

Returning to decision block 163, if the range was not exceeded the last time, the noise index is set to a low value (zero) for the same reason. Thereafter, or if the signal did not indicate pen movement beyond the allowable range, a test is made to determine if the channel is one of the eight loudest channels. If the channel is one of the eight loudest channels, the program proceeds to block 174 where pen frequency ($PF_i$) and pen volume ($PV_i$) control signals are determined based on the noise index value computed in block 160.

Figure 6A:
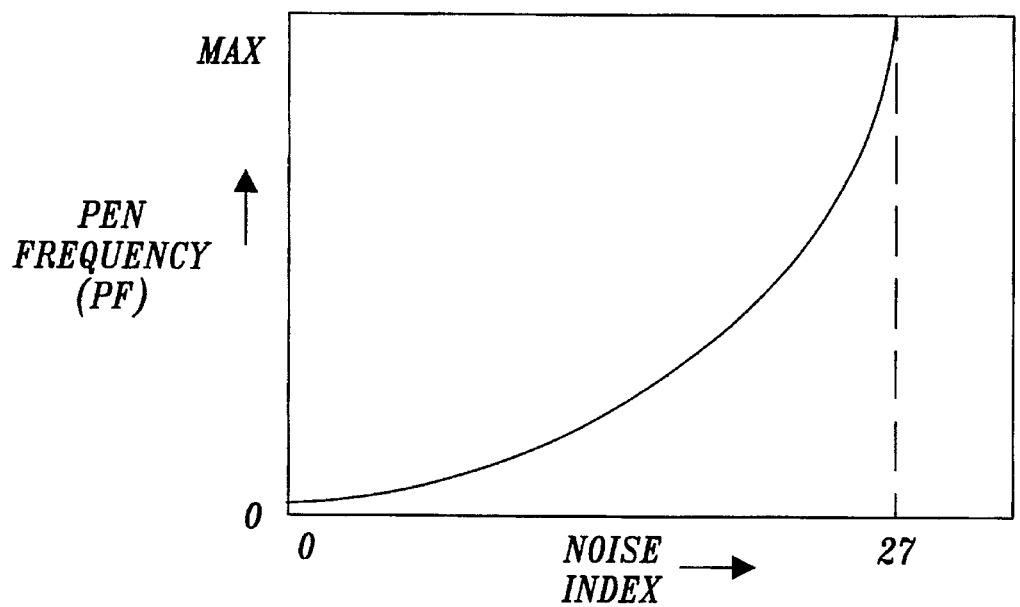
FIGS. 6A and 6B are graphs of look-up tables for the volume and frequency parameters that are used to create signals used to generate the noise of a pen moving across chart paper.
Figure 6B:
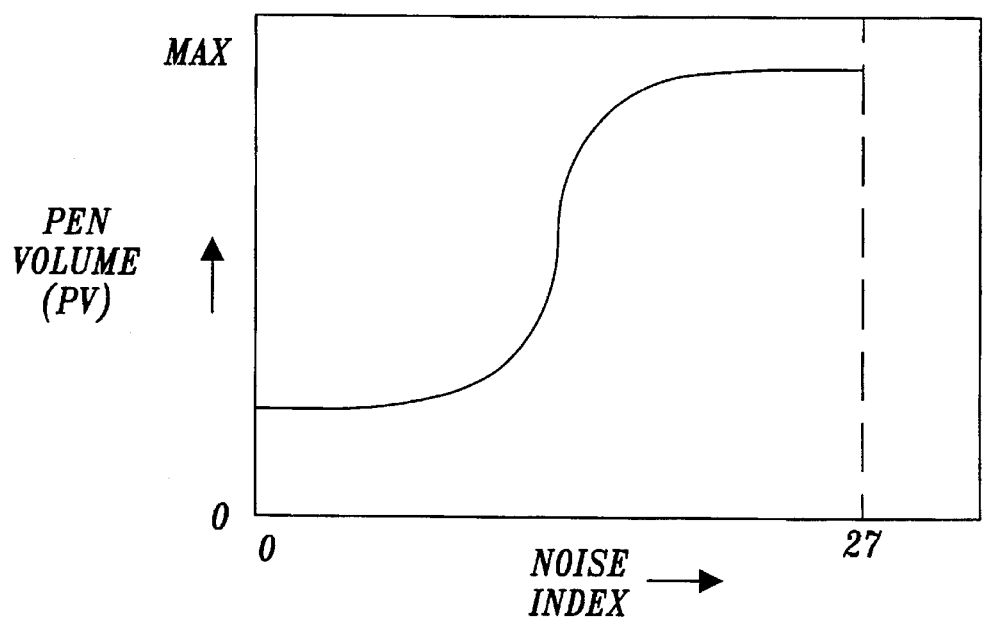

The $PF_i$ and $PV_i$ values are derived from look-up tables. The look-up tables used in this step are illustrated graphically in FIGS. 6A and 6B. FIG. 6A shows that a logarithmic relationship exists between the calculated noise index and the pen frequency ($PF_i$) value. FIG. 5B shows that a sigmoidal relationship exists between the noise index and pen volume ($PV_i$) value. Both look-up tables were experimentally determined by matching the sound produced by the pen of a pen-on-paper EEG recorder when driven by a known signal with the sound produced by a channel 60a of a pen-on-paper synthesizer 52 driven by the same signal. From each look-up table, a given value of the calculated noise index returns a single value for each parameter, i.e., a single value for $PV_i$ and a single value for $PF_i$.

Returning to FIG. 5, after determining the $PV_i$ and $PF_i$ values (block 174), the multiplier 56a and filter 58a of the first pen-on-paper synthesizer channel 60a are reinitialized using the $PV_i$ and $PF_i$ values (block 176). The program then steps to decision block 178, where a check is made to see if all of the eight loudest channel signals have been analyzed. (The program bypasses the foregoing steps and steps to the same block if the channel was not one of the eight loudest channels.) If all of the eight loudest channel signals have not been analyzed, the program loops to block 156, where the next channel is selected, and then to block 158, where the next channel signal is analyzed to determine the speed a pen driven by that signal would have if the signal were applied to the pen of a pen-on-paper EEG recorder.

After generating the signals required to create pen sounds for each of the ten loudest channels (decision block 178), the program determines the next motor noise coefficient value (block 180). The noise of the paper feed mechanism has been experimentally determined to consist of a 50 or 60 Hz fundamental frequency plus harmonics that are smoothly modulated at about 0.5 Hz. To replicate this modulation, the value of the variable coefficient of filter 96 (A1), called the motor noise coefficient (MNC) value, is linearly increased and decreased approximately once every two seconds, i.e., the coefficient value linearly increases from a low value to a high value and then linearly decreases back to the low value approximately once every two seconds (0.5 Hz). The preferred low value range is −0.985 to −0.987 (preferably −0.986) and the preferred high value range is −0.987 to −0.988 (preferably −0.987). After determining the coefficient value, it is used to control the state of the filter 96 of the motor and drive train synthesizer (block 182).

As will be readily appreciated from the foregoing description, the three component synthesizers, i.e., the pen-on-paper synthesizer, the pen-clicking synthesizer, and the motor and drive train synthesizer simulate the sound of a mechanical pen-on-paper EEG recorder. By mimicking the sound of a mechanical system, the invention can be used to restore auditory information to digital EEG systems, allowing medical technicians to once again use this valuable auditory information to assist in monitoring the state of a patient.

While a preferred embodiment of the invention has been illustrated and described, it will be appreciated that various changes can be made therein without departing from the spirit and scope of the invention. In this regard, the major subsystems of the invention can be embodied other than as disclosed. For example, filters, other than digital 2-pole elliptic IIR filters, could be used if desired. Some examples of other suitable filters are FIR filters, lattice filters, nonelliptic IIR filters, voltage-controlled analog gain filters. As with the illustrated filter, the attributes of the analyzed EEG signals are used to determine the coefficients or parameters of the chosen filter type. Further, while the disclosed embodiment contemplates an entirely digital construction, various parts of the component synthesizers, or even the entire synthesizer, could be conceivably reproduced in analog form. Or the continuous noise of the paper feed mechanism could be produced using analog techniques, while pen noise could be produced digitally and then converted before summing. In such embodiments of the invention, prerecorded or presynthesized sounds stored in programmable read only memories (PROMs) or similar memories in either direct or compressed form could be "looked-up" using the attributes of the analyzed EEG signals. Or musical synthesizers (MIDI), voice synthesizers, or sound generator boards can be used, again, with the attributes of the analyzed EEG signals being used to control the parameters of the chosen synthesizer. Hence, within the scope of the appended claims, it is to be understood that the invention can be practiced otherwise than as described herein.

The embodiments of the invention in which an exclusive property or privilege is claimed are defined as follows:

1. In a digital EEG system wherein EEG signals are displayed on a nonaudible display, the improvement comprising an electronic noise synthesizer generating audible sounds, concurrent with display of the EEG signals on the nonaudible display, that correspond to the sounds that would have been produced by a pen-on-paper EEG recorder if the EEG signal had been applied to a pen-on-paper EEG recorder.

2. The improvement claimed in claim 1 wherein said noise synthesizer comprises:

(a) control means for: (i) receiving EEG signals; (ii) determining the path of travel that would be followed by the recorder pens of a pen-on-paper EEG recorder if the EEG signals were applied to a pen-on-paper EEG recorder; and (iii) using the path of travel information to produce pen-on-paper and pen-clicking synthesizer control signals;

(b) a pen-on-paper synthesizer for: (i) receiving said pen-on-paper synthesizer control signals; and (ii) based on said pen-on-paper synthesizer control signals, producing sounds similar to the sounds that would have been made by the pen of a pen-on-paper EEG recorder moving across the paper of the recorder if the EEG signals used to create the pen-on-paper synthesizer control signals had been applied to the recorder; and (c) a pen-clicking synthesizer for: (i) receiving said pen-clicking synthesizer control signals and (ii) based on said pen-clicking synthesizer control signals, producing sounds similar to the sounds that would have been made by the pen of a pen-on-paper EEG recorder colliding with a mechanical stop as the pen moves across the paper of the recorder if the EEG signals used to create the pen-clicking synthesizer control signals had been applied to the recorder.

3. The improvement claimed in claim 2 wherein said pen-clicking synthesizer includes a plurality of channels, each of said channels including a signal generator and a signal modifier for: (i) receiving a pen-clicking synthesizer control signal based on the pen path of travel information derived from a single EEG signal; and (ii) based on said pen-clicking synthesizer control signal, controlling the signal produced by said signal generator and modified by said signal modifier so as to produce a signal that when output creates a sound that replicates the sound that would have been produced by the pen of a pen-on-paper EEG recorder colliding with a mechanical stop if the EEG signal used to create the pen-clicking synthesizer control signal has been applied to the recorder.

4. The improvement claimed in claim 3 wherein said pen-on-paper synthesizer includes a plurality of channels, each of said channels including a signal generator and a signal modifier for: (i) receiving a pen-on-paper synthesizer control signal based on the pen path of travel information derived from a single EEG signal; and (ii) based on said pen-on-paper control signal, modifying the signal produced by said signal generator so as to produce a signal that when output creates a sound that replicates the sound that would have been produced if said EEG signal had been applied to the pen of a pen-on-paper EEG recorder.

5. The improvement claimed in claim 4 wherein said control means also produces motor and drive train synthesizer control signals and wherein said noise synthesizer also includes a motor and drive train synthesizer for: (i) receiving said motor and drive train synthesizer control signals; and (ii) based on said motor and drive train synthesizer control signals, produces sounds similar to the sounds produced by the motor drive train of a pen-on-paper EEG recorder.

6. The improvement claimed in claim 4 wherein said noise synthesizer further comprises: a summer for summing the signals produced by said pen-on-paper synthesizer, said pen-clicking synthesizer; and said motor and drive train synthesizer; a digital-to-analog converter for converting the signals summed by said summer into analog form; and an audio output means for producing an audio output based on the signal produced by said digital analog converter.

7. The improvement claimed in claim 2 wherein said pen-on-paper synthesizer includes a plurality of channels, each of said channels including a signal generator and a signal modifier for: (i) receiving a pen-on-paper synthesizer control signal based on the pen path of travel information derived from a single EEG signal; and (ii) based on said pen-on-paper control signal, modifying the signal produced by said signal generator so as to produce a signal that when output creates a sound that replicates the sound that would have been produced if said EEG signal had been applied to the pen of a pen-on-paper EEG recorder.

8. The improvement claimed in claim 7 wherein said control means also produces motor and drive train synthesizer control signals and wherein said noise synthesizer also includes a motor and drive train synthesizer for: (i) receiving said motor and drive train synthesizer control signals; and (ii) based on said motor and drive train synthesizer control signals, produces sounds similar to the sounds produced by the motor drive train of a pen-on-paper EEG recorder.

9. The improvement claimed in claim 8 wherein said noise synthesizer further comprises: a summer for summing the signals produced by said pen-on-paper synthesizer, said pen-clicking synthesizer, and said motor and drive train synthesizer; a digital-to-analog converter for convening the signals summed by said summer into analog form; and an audio output means for producing an audio output based on the signal produced by said digital-to-analog converter.

10. The improvement claimed in claim 2 wherein said control means also produces motor and drive train synthesizer control signals and wherein said noise synthesizer also includes a motor and drive train synthesizer for: (i) receiving said motor and drive train synthesizer control signals; and (ii) based on said motor and drive train synthesizer control signals, produces sounds similar to the sounds produced by the motor drive train of a pen-on-paper EEG recorder.

11. The improvement claimed in claim 10 wherein said noise synthesizer further comprises: a summer for summing the signals produced by said pen-on-paper synthesizer, said pen-clicking synthesizer, and said motor and drive train synthesizer; a digital-to-analog converter for converting the signals summed by said summer into analog form; and an audio output means for producing an audio output based on the signal produced by said digital-to-analog converter.

\* \* \* \* \*

UNITED STATES PATENT AND TRADEMARK OFFICE
CERTIFICATE OF CORRECTION

PATENT NO. : 5,566,678
DATED : October 22, 1996
INVENTOR(S) : J.A. Cadwell

It is certified that error appears in the above-indentified patent and that said Letters Patent is hereby corrected as shown below:

| COLUMN | LINE | |
|---|---|---|
| 11 (Claim 6, | 17 line 4) | After "synthesizer" delete ";" and insert therefor --,-- |
| 12 (Claim 9, | 12 line 5) | "convening" should read --converting-- |

Signed and Sealed this

Twenty-sixth Day of May, 1998

Attest:

BRUCE LEHMAN

*Attesting Officer*  *Commissioner of Patents and Trademarks*

REEXAMINATION CERTIFICATE (3942nd)

United States Patent [19]
Cadwell

[11] B1 5,566,678
[45] Certificate Issued Nov. 30, 1999

[54] DIGITAL EEG NOISE SYNTHESIZER

[75] Inventor: John A. Cadwell, Richland, Wash.

[73] Assignee: Cadwell Industries, Inc., Kennewick, Wash.

Reexamination Request:
No. 90/004,539, Feb. 9, 1997

Reexamination Certificate for:
Patent No.: 5,566,678
Issued: Oct. 22, 1996
Appl. No.: 08/369,270
Filed: Jan. 5, 1995

Related U.S. Application Data

[63] Continuation of application No. 08/119,955, Sep. 10, 1993.
[51] Int. Cl.$^6$ ....................................................... A61B 5/04
[52] U.S. Cl. ........................... 600/544; 600/545; 600/546
[58] Field of Search ........................................... 600/544–6

[56] References Cited

U.S. PATENT DOCUMENTS 5,101,220   3/1992   Sullivan .

*Primary Examiner*—Robert L. Nasser, Jr.

[57] ABSTRACT

A method and apparatus for generating an audio accompaniment for digital EEG systems (electroencephalographs) is disclosed. In the past, EEG systems included pen-on-paper EEG recorders to trace a representation of sensed brain wave activity on a strip of paper. This produced varying amounts of auditory noise that corresponded to the amount of brain wave activity which was used by medical technicians monitoring a patient. Digital EEG systems create traces on non-auditory (i.e., CRT) displays. As a result, the auditory feedback provided by the movement of pens on paper and the associated medical benefits have been lost. The invention remedies this problem by providing a method and apparatus that analyzes EEG signals and mimics the sounds that would have been created by the prior art pen-on-paper EEG recorders if the signals had been applied in analog form to such recorders. The invention includes several different synthesizers that replicate the sounds of pens moving across recorder paper, pens hitting on one another, and the motor drive train of a pen-on-paper EEG recorder. The system constantly analyzes the incoming EEG signals and updates control signals that control the synthesizers in a way that ensures that the sounds produced closely approximate the sounds of an equivalent pen-on-paper EEG system.

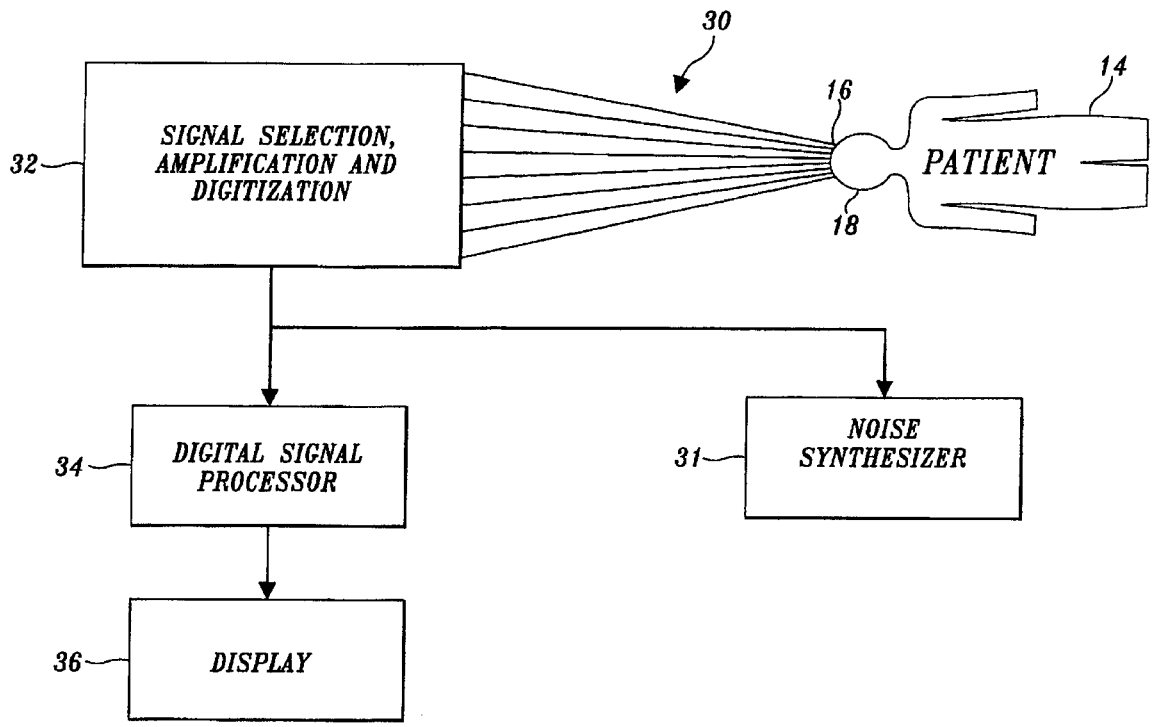

REEXAMINATION CERTIFICATE ISSUED UNDER 35 U.S.C. 307

THE PATENT IS HEREBY AMENDED AS INDICATED BELOW.

AS A RESULT OF REEXAMINATION, IT HAS BEEN DETERMINED THAT:

Claims 1–11 are cancelled.

\* \* \* \* \*